United States Patent [19]
Vilkomerson

[11] 3,953,822
[45] Apr. 27, 1976

[54] WAVE-ENERGY IMAGING TECHNIQUE

[75] Inventor: David Herman Raphael Vilkomerson, South Brunswick Township, Middlesex County, N.J.

[73] Assignee: RCA Corporation, New York, N.Y.

[22] Filed: Oct. 15, 1973

[21] Appl. No.: 406,218

[52] U.S. Cl. ........................... 340/1 R; 73/67.7; 340/5 MP; 343/17; 356/106 R; 340/15.5 DS
[51] Int. Cl.² .................... G01S 7/04; G01S 7/56
[58] Field of Search ............... 340/5 MP, 5 H, 1 R, 340/15.5 DS; 343/17; 356/106 R; 73/67.5 R, 67.5 H, 67.7

[56] References Cited
UNITED STATES PATENTS

| | | | |
|---|---|---|---|
| 3,617,994 | 11/1971 | Glenn, Jr. et al. | 340/5 H |
| 3,771,116 | 11/1973 | Farrah | 343/17 |

*Primary Examiner*—Richard A. Farley
*Attorney, Agent, or Firm*—Edward J. Norton; George J. Seligsohn

[57] ABSTRACT

A circumferential array of $n$ transducers is used to image an object with resolution equal to that of an array over the entire bounded aperture. This is done by illuminating the object with $m$ components of coherent wave energy, and coherently detecting the signal picked up by each of the $n$ transducers for each of the $m$ wave energy components to provide the coefficients of $m$ complex numbers for each of the $n$ transducers. Signal processing these coefficients, in the manner described in the disclosure, permits an image of the object to be displayed on a display device with resolution equal to that of an array filling the aperture.

15 Claims, 6 Drawing Figures

WAVE ENERGY OBJECT IMAGING SYSTEM

ACOUSTIC COUPLING UNIT FOR IMAGING
INTERNAL ORGANS OF HUMAN BODY

SEISMIC OBJECT IMAGING

MICROWAVE OBJECT IMAGING

Fig. 5. OPTIC OBJECT IMAGING

WAVE-ENERGY IMAGING TECHNIQUE

This invention relates to a wave-imaging technique, and, more particularly, to such a technique which is suitable for imaging the internal structure of an object illuminated with coherent wave energy.

The term "wave energy", as used herein, includes any type of electromagnetic wave energy or acoustic wave energy.

The conventional way to obtain an image of an object illuminated with wave energy is to employ a physical lens or combination of lenses situated in the path of the portion of the illuminating wave energy that has been reflected from (or transmitted through) the object. An imaging lens operates by phase shifting the wave energy arriving at any point thereof by an amount which is a given function of the geometric position of that point in the lens aperture. Thus, the conventional convex lens provides a maximum phase shift to wave energy incident at the center of the lens, where the lens is thickest, and a minimum phase shift to wave energy incident at a point on the periphery of the lens, where the lens is thinnest. One undesirable characteristic of a physical imaging lens is that it inherently exhibits aberrations at some ray angles.

In principle, at least, a physical imaging lens can be replaced by a synthetic lens for effectively performing the aforesaid phase-shifting function required for imaging, without introducing the aberrations of a physical lens. For instance, if a sufficient number of coherent wave energy detectors were to receive signals from respective predetermined points distributed over an aperture area illuminated with an object information beam of wave energy, each one of the coherent detectors would sample the relative amplitude and phase of the wave energy incident at that predetermined point of the aperture at which it is located. Now, if the output from each individual one of these coherent detectors is effectively phase-shifted by its own proper amount (depending upon its particular location in the aperture), a distribution of signals defining the same image wavefront as that emerging from a corresponding physical imaging lens would be obtained. Such a synthetic imaging lens can take the form of analog and/or digital signal processing means. The output from such a signal processing means, which defines the image of the object information, can be used (1) to generate a physical imaging wavefront of wave energy which would form an image in an image plane, or (2) the output from the image-lens signal processing means could be further processed to display the image of the object information on such means as a cathode ray tube screen.

Unfortunately, a synthetic imaging lens of the type outlined above is not practical because of the very large number of sample points (each with its own coherent detector and effective phase shifter) it would require. Specifically, as is known, image resolution depends upon the size of the aperture with respect to the wavelength of the wave energy employed. In order to obtain reasonably good image resolution, an aperture diameter in the order of 100 wavelengths of wave energy is needed. Based on the formula for the area of a circle, an aperture of such size consists of more than 7800 elemental areas each of one square wavelength. Each of these elemental areas would require its own coherent detector and its own effective phase shifter. From a practical point of view this very large number of sampling points would be very difficult and uneconomically expensive to implement.

The present invention is directed to a modification of the above-described synthetic imaging system, and requires a number of sampling points proportional only to the circumference of the aperture, rather than the area thereof. This reduces the number of sampling points to a number which permits implementation of the invention for various useful purposes, to be described below, at reasonable cost. By way of example, the more than 7800 sample points, discussed above, is reduced by a factor of 25 to 314 by employing the principles of the present invention.

In a concept developed for radio-astronomy, J. P. Wild and his co-workers have shown, both theoretically and experimentally, that the signals from a circumferentially distributed array of antennas can be processed to provide an image of luminous radio-wave energy sources whose energy falls upon the aperture of such a circumferential antenna array with the same resolution as that which is obtainable from the type of an array in which the antennas are distributed over the entire area of the aperture, with the spacing between adjacent antennas being the same for both types of arrays (*Proceedings of the Royal Society*, Volume 262, page 84; Volume 263, page 545; Volume 286, page 499 and Nature, Volume 218, page 536). Thus, Wild has found that the resolution obtained from his circumferential array of antennas (known as the Culgoora radioheliograph) was as high as that obtainable from an area array of antennas, despite the fact that the total number of antennas in the area array is much larger than that in the circumferential array. Because each antenna of an array contributes essentially the same proportion of the total power of array, the sensitivity of an array (which contains more individual antennas) is higher than that of a Culgoora radioheliograph of the same resolution capability.

More specifically, Wild shows in his papers that the full aperture resolution can be obtained from the circumferential signals around the aperture by adding progressive phase shifts to the signals, where the phase shifts are a function of position of the aperture. That is, if a particular signal detector is at $\theta = 1$ radian, the signal is first taken with no phase shift added, then taken with the addition of one radian phase shift 2 radians, etc., up to, say 20 radians (the more terms taken the higher the accuracy of the image). As more fully explained in Wild's papers, Wild's procedure is to add the progressive phase shift to obtain Bessel functions of different order and then properly weigh the square of the Bessel functions to obtain the image. In this manner, the image formed by the various corrected summed signals is that which would have been obtained if the array were distributed over the full area of the aperture, rather than only about the circumference thereof.

It is essential to the operation of Wild's procedure that the effective object distance to the source of the wavefront incident on the circumferential array be infinite (i.e., the incident wavefront be substantially a plane wavefront) and the the source of the wavefront be effectively incoherent. Both of these conditions are fulfilled in the radio astronomical cases considered by Wild, where the objects to be imaged are luminous astral bodies.

In the case of the present invention, the wavefront incident on the circumferential array comes from a nearby object which reflects or transmits coherent wave energy when it is illuminated. In the case of coherent illumination, the number of degrees of freedom in the image (i.e. how many independent image points can be obtained) is given by the number of detectors in the array, while with incoherent illumination the degrees of freedom is obtained by the number of detectors squared (*Journal of the Optical Society of America*, Volume 59, page 799). Thus, neither of the two conditions essential to Wild's procedure exists in the case with which the present invention is concerned.

However, in accordance with the present invention, the image formation method based on sums of Bessel functions, as proposed and demonstrated by Wild, can be used for a nearby object illuminated with coherent wave energy by (1) employing signal-processing means including a synthetic lens, of a type to be described below, for transforming the object plane to infinity and (2) destroying the effects of coherence by providing signal processing means which either store the sum of multiple "exposures" of the array in which the phase relations between points on the objects for each successive exposure is different (as could be accomplished by a movement of a diffuser in the illuminating path) or, alternatively, simultaneously processing in parallel each of a plurality of different predetermined wave energy frequencies, all of which are included in the wave energy illuminating the object. With these modifications, practical acoustic imaging and electromagnetic imaging systems can be implemented.

These and other features and advantages of the present invention will become more apparent from the following detailed description, taken together with the accompanying drawing, in which.

Figure 1:
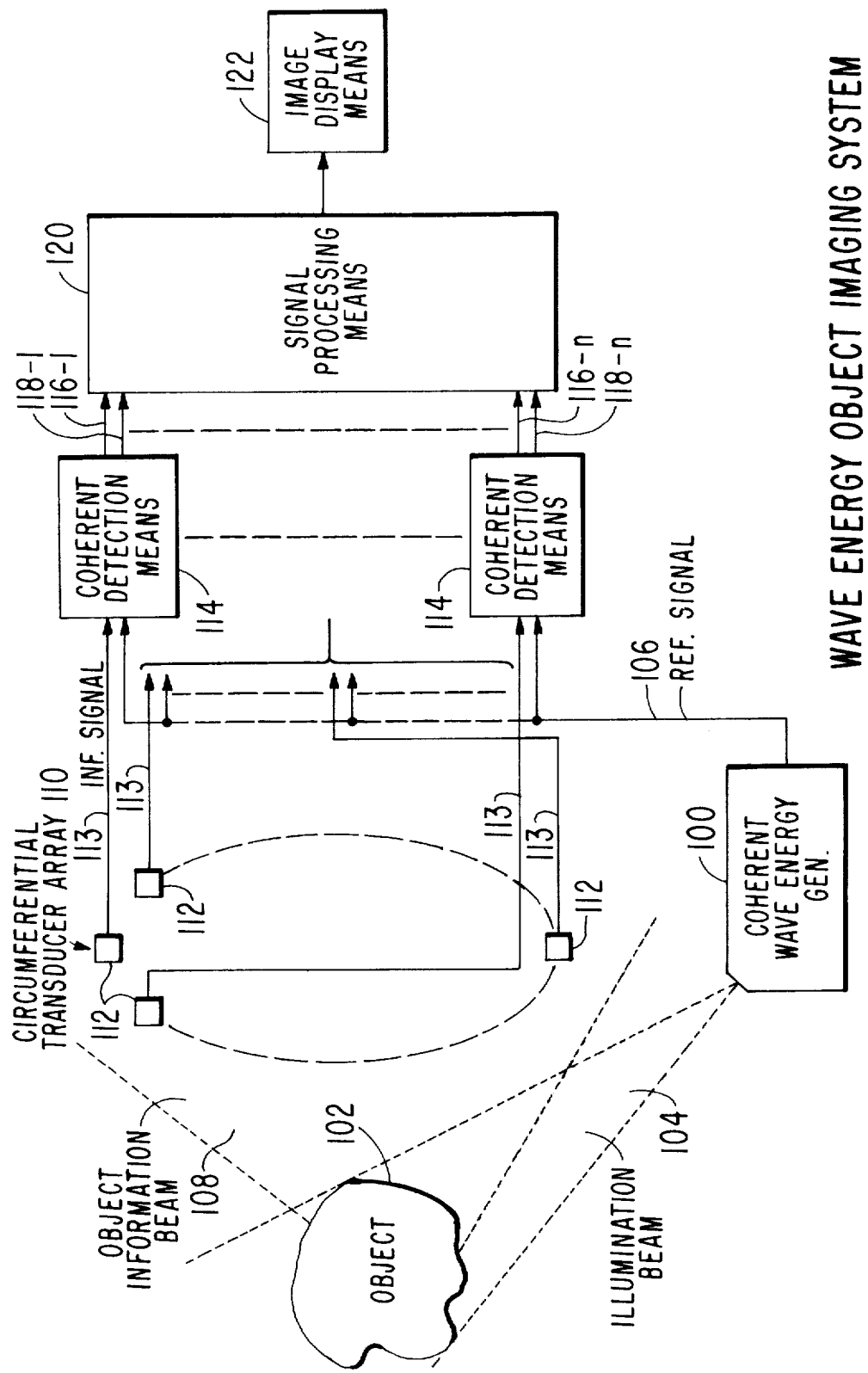
FIG. 1 is an illustrative block diagram of a wave energy object imaging system employing the principles of the present invention.

As shown in FIG. 1, any type of wave energy object imaging system incorporating the principles of the present invention includes a coherent wave energy generator 100 for illuminating an object 102, which is to be imaged by the system, with an illuminating beam 104 of coherent wave energy. Alternatively, illuminating beam 104 may either consist of substantially a single preselected frequency of diffused coherent wave energy or the sum of a predetermined plural number of different preselected frequencies of coherent wave energy. Coherent wave energy generator 100 also generates a reference signal 106 composed of the same frequency or frequencies contained in illuminating beam 104.

In response to the illumination thereof by illuminating beam 104, object 102 reflects (or transmits) object information beam 108 of wave energy.

Located at a predetermined distance from object 102 in the path of object information beam 108 is circumferential transducer array 110 composed of a plurality of individual transducers 112 situated at equally spaced points on the circumference of a circle of given diameter. Typically, the diameter of the given circle will be at least 100 wavelengths of the wave energy illuminating object 102. However, the diameter of circumferential transducer array 110 may be even less than 100 wavelengths in those cases where a relatively poor image resolution will suffice.

Each respective one of transducers 112 converts the wave energy impinging thereon into a corresponding information signal having a phase and amplitude determined by the phase and amplitude of the impinging wave energy. Associated with each individual transducer 112 of circumferential transducer array 110 is a respective one of coherent detection means 114. Information signal 113 from each transducer 112 is applied as a first input to its associated coherent detection means 114. Thus, if circumferential transducer array 110 has a diameter of 100 wavelengths and transducers 112 are spaced at one-wavelength intervals from each other, there will be a total of 314 transducers 112 in array 110 and, associated therewith, would be a group of 314 coherent detection means 114. Reference signal 106 is supplied in common as a second input to all of the coherent detection means 114 in the group.

In the case where the illuminating wave energy includes only a single predetermined frequency, each of coherent detection means 114 includes two phase detectors and a 90° phase shifter. The first of the phase detectors has the information and reference signals for that coherent detection means applied directly as inputs thereto and the other of the phase detectors has these signals applied to inputs thereof only after one of them has been shifted in phase by 90° by the phase shifter of that coherent detection means. Such coherent detection means, as known in the art, produce two respective outputs (one from each of the two phase detectors thereof), corresponding respectively to real and imaginary coefficients of a complex number having respective values determined by the amplitude and phase of the wave energy impinging on the transducer with which that coherent detection means is associated.

As shown in FIG. 1, the group of coherent detection means 114 is arranged in an orderly way with respect to the transducers 112 of array 110 with which they are associated. In particular, if the transducers are considered in order starting with the top transducer 112 and proceeding in a clockwise direction around the circumference of array 110, the first coherent detection means 114 of the group, counting from the top, is associated with the top transducer 112, and then in order so that the last coherent detection means 114 of the group is associated with the transducer 112 adjacent the top transducer in a counter-clockwise direction, as shown in FIG. 1. Assuming a total of $n$ transducers and associated coherent detection means, the respective real and imaginary outputs from the first coherent detection means 110 of the group are designated as 116—1 and 118—1 and the respective real and imaginary outputs from the last coherent detection means 114 of the group are designated 116—$n$ and 118—$n$.

In the case where the illuminating wave energy consists of only a single frequency, each of connections 116—1 . . . 116—$n$ and each of connections 118—1 . . . 118—$n$ consists of a single output on a single conductor. However, in the case where the illuminating wave energy consists of a predetermined plural number of frequencies, such as $m$, each coherent detection means includes frequency filters for both the information signal and reference signal to provide $m$ channels, one for each of the respective $m$ frequencies. Each of these $m$ channels is provided with its own first and second phase detectors and 90° phase shifter. In this case, each coherent detection means provides $m$ pairs of real and imaginary outputs, so that each of connections 116—1 . . . 116—$n$ and each of connections 118—1 . . . 118—$n$ is a cable of $m$ conductors. Each of these conductors couples a separate and distinct corresponding output from the coherent detection means 114 of the group as a separate and distinct input signal to signal processing means 120.

In the latter case, where the illuminating beam consists of a predetermined plural number of $m$ coherent frequencies, only a single exposure of object 102 by illuminating beam 104 is required. However, in the former case, where object 102 is illuminated by illuminating beam 104 consisting of a single diffused frequency, it is necessary that object 102 be sequentially exposed a predetermined plural number of times, such as $m$, with the diffusion of illuminating beam 104 being altered between each two successive exposures. The respective values of the real and imaginary outputs appearing on each of connections 116—1 . . . 116—$n$ and 118—1 . . . 118—$n$, is different for each separate exposure. Thus, for the total series of $m$ exposures, signal processing means 120 receives as many separate pieces of information from the group of coherent detection means 110 as in a single exposure in the case where coherent wave energy generator 100 simultaneously generates an illuminating beam 104 of wave energy having a predetermined plural number of different coherent frequencies. Thus, in both cases, each coherent detection means 114 provides signal processing means 120 $m$ pieces of information over its 116 connection and $m$ pieces of information over its 118 connection, regardless of whether this information is applied in parallel or in series. Therefore, signal processing means 120 receives a total of $2mn$ separate pieces of information from the group of coherent detection means 114. This information is sufficient to define an image of object 102 of resolution equal to that obtained by use of detectors over the entire aperture of the circle bounded by array 110. However, in order to actually obtain this image, it is necessary for signal processing means 120 to properly process the information.

Preferably signal processing means 120 comprises analog-to-digital converters responsive to the respective real and imaginary analog values of the inputs to signal processing means 120 present on connections 116—1 . . . 116—$m$ and 118—1 . . . 118—$m$, and a digital computer programmed in a manner described below to process the signals. However, signal processing means 120 may include purely analog means or any combination of analog and digital means for performing this same purpose, rather than a digital computer.

As is known in optical imaging, every point in the object plane within the aperture of the imaging system has a corresponding point in the image plane. Although in principle all the image points could be processed simultaneously in parallel, this would take a much larger computer than is required if each point of the image is processed separately in serial order.

The computer has certain given parameters and certain measured parameters available to it for computing the image. Among the given parameters is the nominal distance between the object plane in which object 102 is located and the plane of transducer array 110, as well as the co-ordinates of each sample point in the object plane. The measured parameters comprise the real and imaginary values of the inputs to signal processing means 120 from coherent detection means 114. In particular, the arc tangent of the phase angle of the wave energy picked up by any one of the transducers 112 is proportional to the ratio of the imaginary output to the real output from the coherent detection means 114 associated with that one transducer and the amplitude of the wave energy picked up by any one transducer 112 is proportional to the square root of the sum of the squares of the respective imaginary and real outputs of the coherent detection means 114 associated with that one transducer.

Considering a single sample point of the object plane whose energy falls within the aperture of the array, there is a set of phase shifts individually corresponding with each of transducers 112, which if subtracted from the measured phase of the output signal from that transducer, in effect transforms that sample point to the same corresponding sample point in a virtual object plane situated an "infinite" distance from the plane of transducer array 110. (The term infinite, as used herein, means that the size of the diameter of the array is negligible compared to the effective distance between the array and the virtual (infinitely distant) object plane.) Signal processing means 120 further processes the signals corresponding with the then-selected sample point in accordance with the Bessel function summing technique of Wild, discussed above, to obtain a signal manifesting the image sample point having co-ordinates corresponding with the then-selected object sample point. This image sample point signal is then stored at a storage location corresponding with its coordinates. By repeating this entire process for each separate sample point in the object plane within the aperture of array 110, the entire image is stored. An image display means 122, such as a cathode ray tube, which has a unique display point addressable from and bearing a one-to-one correspondence with each stored image point, manifests the image of object 102 to a viewer.

Figure 6:
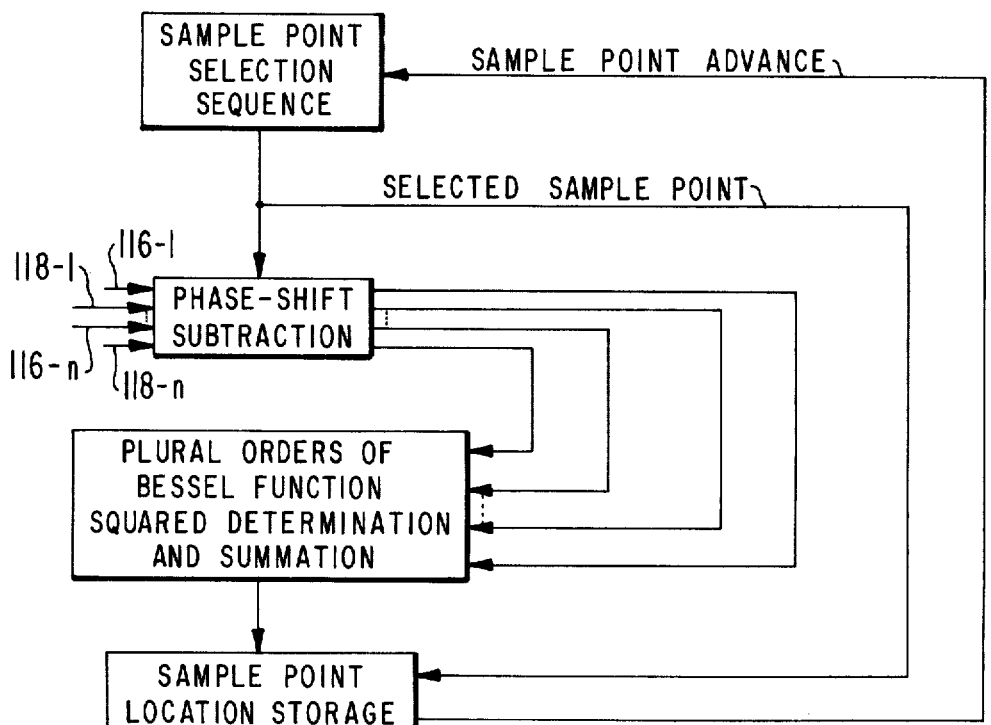
FIG. 6 is a flow sheet illustrating the signal processing steps which take place within signal processing means 120 of FIG. 1.

The signal processing steps just described are illustrated in the signal processing flow sheet of FIG. 6. In particular, a sample point selection sequence designates each successive selected sample point in turn. In accordance with information designating the selected sample point, a predetermined phase-shift subtraction is made to the respective complex outputs 116—1 . . . 116—$n$ and 118—1 . . . 118—$n$ from the coherent detection means 114. This phase-shift subtraction modifies the phase of these respective outputs so that, in effect, the modifie components corresponding only to the selected sample point is equivalent to what these components would have been if the sample point actually had been situated at an infinite distance from the plane of transducer array 110. Information as to the sample point then selected by the sample point selection sequence is also employed to address an appropriate sample point location storage area corresponding to that selected sample point in the virtual object plane situated an infinite distance from the plane of transducer array 110. Therefore, when the phase-shift subtracted signals corresponding to the selected sample point are further processed to provide plural orders of Bessel function squared determination and summation, in the manner described in Wild's papers, a signal corresponding to the wave energy intensity at the sample point is stored at the appropriate sample point location storage. After this has been accomplished, the sample point selection sequence is advanced to designate the next selected sample point in the sequence and the whole process is repeated.

Due to the fact that coherent wave energy is employed, the displayed image from a single exposure of single-frequency diffused coherent wave energy results in a displayed image exhibiting a great deal of "speckle" noise. However, sequential multiple exposures, with the image signals for each sample point being summed or averaged in the image store of signal processing means 120, for that sample point, results in the speckle noise in the displayed image being eliminated, if the diffusion of the coherent wave image is altered between successive exposures. In a similar manner, the summing or averaging of the corresponding image points for each of the plurality of separate channels utilized when coherent wave energy generator 100 provides a multi-frequency illuminating beam, also results in overcoming the deleterious effects of coherence on image resolution.

The generalized wave energy object imaging system of FIG. 1 is of particular utility when employed in any of the embodiments shown in FIGS. 2–5.

One of the most important applications of the present invention is as a diagnostic medical instrument in which the relatively soft internal organs of the human body may be imaged with good resolution. In this case, the body is illuminated with ultrasonic acoustic wave energy, where the frequency of this acoustic wave energy is usually between 1.0 and 1.5 MHz. The illuminating acoustic wave energy is reflected from boundaries between different types of tissue having different acoustic transmission characteristics. A circumferential acoustic transducer array receiving this reflected wave energy, by employing the techniques of the present invention, can provide a good resolution image of the illuminated tissue. Such an image would be very helpful in observing the size and shape of a cancer, by way of example.

Figure 2:
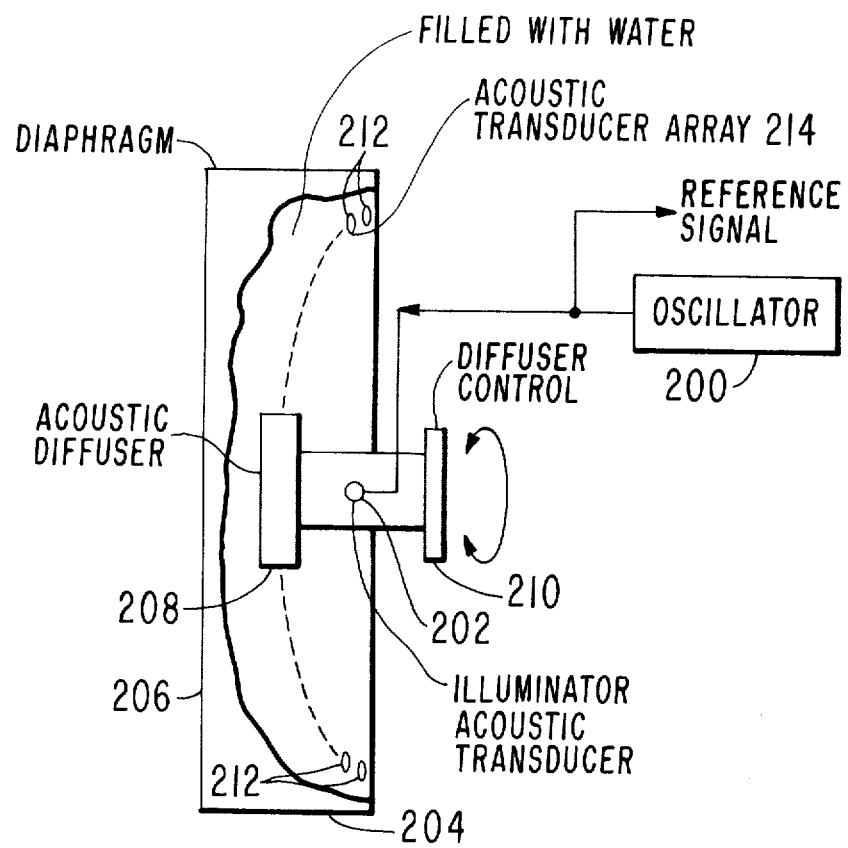
FIG. 2 shows an acoustic coupling unit for imaging internal organs of the human body for use in a first embodiment of the present invention.

FIG. 2 shows an acoustic coupling unit for such a system coupled to a wave energy source. In particular, oscillator 200 generates a sinusoidal signal, which is employed both as a reference signal and as an energizing signal for illuminator acoustic transducer 202. Illuminator acoustic transducer 202 is located as shown in housing 204 which comprises diaphragm 206 situated at a terminating end thereof. Housing 204 is filled with a fluid, such as water, in which illuminator acoustic transducer 202 is immersed. Also immersed in the fluid within the housing 204 is acoustic diffuser 208, which is located, as shown, between illuminator acoustic transducer 202 and diaghragm 206. Diffuser 208 is attached to diffuser control 210 situated on the outside of housing 204. The position of acoustic diffuser 208 may be changed by rotating or otherwise moving diffuser control 210. Also immersed in the fluid of housing 204, and symmetrically disposed about illuminator acoustic transducer 202 on the circumference of a circle, are the respective pickup transducers 212 of a circumferential acoustic transducer array 214. Acoustic transducer array 214 corresponds in function to transducer array 110 of FIG. 1. The signals from acoustic transducer array 214 and the reference signal from oscillator 200 are applied to coherent detection means, signal processing means and image display means of the type discussed in detail with connection to FIG. 1.

The diameter of diaphragm 206 of the acoustic coupling unit shown in FIG. 2 may be in the order to 5 inches or so. In practice, diaphragm 206 is placed against an area of the skin of the human body with diffuser control 210 in a first random position thereof and illuminator acoustic transducer 202 is energized by oscillator 200 for a suitably short period of time, such as a fraction of a second. Diffuser control 210 is moved to another random position and a second similar exposure is made. It can be seen that a series of 10 or 15 exposures can be made within a minute or two without any difficulty so that, essentially in real time, an image of an internal organ of the human body can be obtained and viewed. Furthermore, by moving the acoustic coupling unit to each of several portions of the body after each series of multiple exposures, the internal organ of the human body may be viewed from several different angles in a relatively short period of time without any objectionable discomfort to the patient.

Figure 3:
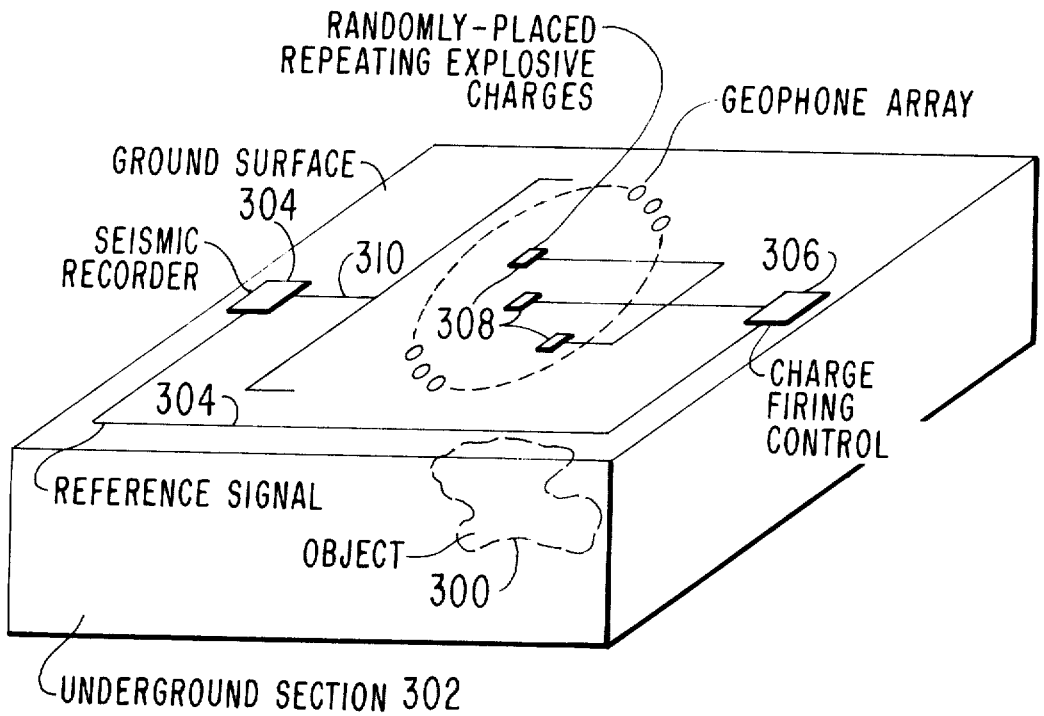
FIG. 3 illustrates a second embodiment of the present invention providing seismic object imaging.

Referring now to FIG. 3, there is shown an application of the present invention to seismic object imaging. Object 300 may be an oil-bearing formation or other geologic formation of interest forming part of underground section 302 of the earth. On the surface of the earth is circumferential geophone array 304, seismic recorder 304, charge firing control 306 and a plurality of randomly-placed repeating explosive charges 308 situated within the aperture defined by a geophone array 302. Each of the repeating explosive charges 308, when fired by charge firing control 306, produces a train of successive explosions which occur at a predetermined repetition rate. This predetermined repetition rate defines the coherent frequency of the seismic wave energy with which object 300 is illuminated. Some of this illuminated wave energy is reflected at the boundary of object 300 back to ground surface and picked up by each of the geophones of geophone array 302. The signals generated thereby are individually applied as information signals to seismic recorder 304 over table 310. Charge firing control 306 derives a reference signal at the coherent frequency of the then exploding repeating explosive charge 308 and applies it over connection 312 to seismic recorder 304. Seismic recorder 304 includes coherent detectors, signal processing means and image display means of the type described in connection with FIG. 1 for displaying an image of object 300.

In the case of seismic object imaging, it is not possible to diffuse the illuminating wave energy in the ground and alter the diffusion of the illuminating wave energy between successive exposures of object 300, in the manner described in connection with FIGS. 1 and 2. However, in the case of seismic object imaging of FIG. 3, a similar effect is obtained by randomly placing the repeating explosive charges 308 and obtaining a series of sequential exposures of object 300 by firing a different set of the randomly-placed repeating explosive charges 308 in turn. In this case, the random placement of the successively exploded repeating explosive charges has the same effect as the change in the diffusion of the illuminating beam between successive exposures in the cases described in connection with FIGS. 1 and 2.

Figure 4:
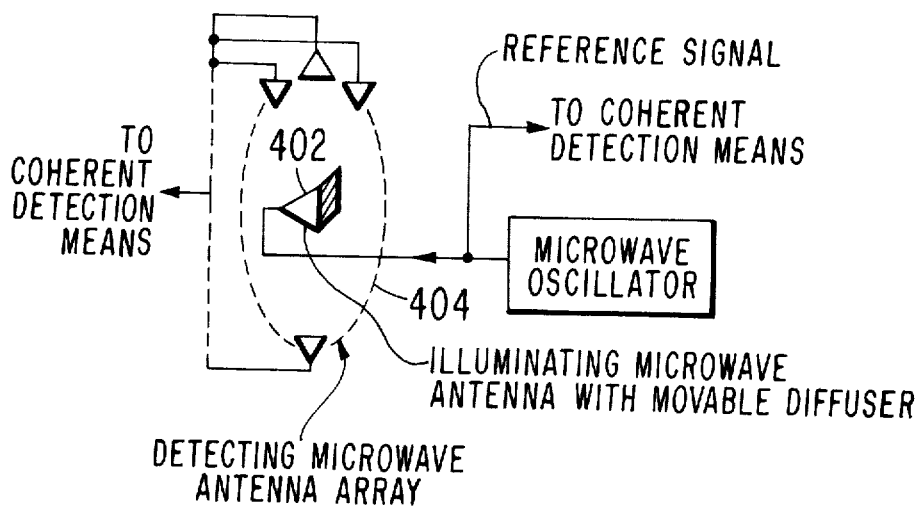
FIG. 4 illustrates a third embodiment of the present invention providing microwave object imaging.

Referring now to FIG. 4, there is shown the arrangement employed for microwave object imaging. Because microwaves penetrate some distance into various mediums, such as the ground, which are visually opaque, and because object formations within such a medium may have a different dielectric constant from its surrounding, the present invention may be employed to utilize microwaves for imaging such an object. In this case, a microwave oscillator 400 generates both an illuminating signal, which is transmitted by illuminating microwave antenna with moveable diffuser 402, and a reference signal. Illuminating antenna 402 is situated at the center of a circumferential detecting microwave antenna array 404. Both the reference signal and the information signals from each of the detecting microwave antennas of array 404 are then supplied to coherent detection means of the type discussed in connection with FIG. 1. As in FIG. 1, the outputs of such coherent detection means are processed by signal processing means as an image of a detected object is displayed by image display means. The series of exposures are taken with the diffuser of antenna 402 moved between peak error sequential exposures.

Figure 5:
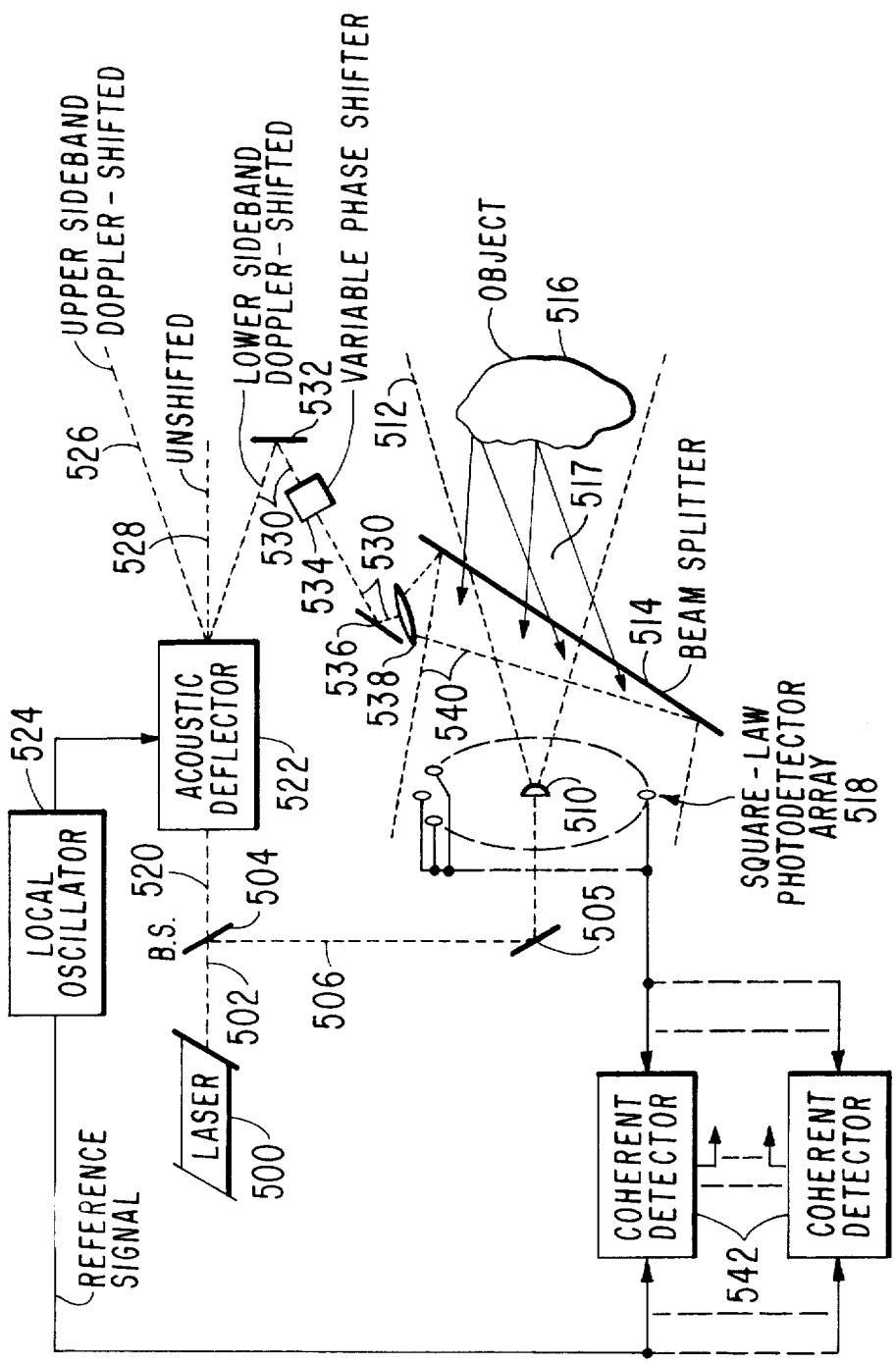
FIG. 5 illustrates a fourth embodiment of the present invention providing optic object imaging.

Referring now to FIG. 5, there is shown an arrangement for optic object imaging, which is particularly useful for non-visible ultra-violet or infra-red light frequencies, where high quality physical imaging lens are difficult or impossible to obtain.

In particular, as shown in FIG. 5, laser 500 generates coherent optic wave energy beam 502, which is incident on beam splitter 504. Reflected from beam splitter 504 is first component beam 506, which after reflection from mirror 505 and expansion by lens 510, forms diverging object-illuminating beam 512. Illuminating beam 512 passes through beam splitter 514 and illuminates object 516. Object 516 reflects diffused coherent wave energy 518, which passes through beam splitter 514 and impinges on the individual photodetectors of square-law photodetectors array 518.

Simultaneously therewith, second component beam 520 passes through beam splitter 504 and is incident on acoustic deflector 522. As is known in the art, acoustic deflector 522, which includes an acoustic transducer operated by a sinusoidal signal of a predetermined frequency from local oscillator 524, alters the optical transmission characteristics of a medium to which beam 520 travels in accordance with the acoustic signal derived from local oscillator 524. The result is that the optical wave energy in beam 520 is modulated at the frequency of local oscillator 524 and emerging from acoustic deflector 522 is an upper sideband doppler shifted deflected component 526, which travels in a first direction (toward the upper right in FIG. 5); an unshifted, undeflected component 528, and a deflected lower sideband doppler-shifted component 530, which travels in a second direction (towards the lower right in FIG. 5). Only lower sideband doppler-shift component 530 is made use of in the present invention. In particular, after being reflected from mirror 532, passing through variable phase shifter 534 and then being reflected from mirror 536, beam 530 is expanded by lens 538 to form diverging beam 540. Diverging beam 540 is reflected from beam splitter 514 and then illuminates the respective square-law photodetectors of array 518.

It should be noted that although FIG. 5 employs physical lenses 510 and 538 for expanding incident light, in neither case does this incident light contain any object information nor are these physical lenses employed for imaging purposes. As is known, the high quality required of imaging lenses is not required of lenses operating on light having no object-information content.

Simultaneous illumination of the photodetectors of array 518 by object-information beam 517 and reference beam 540 results in an interference pattern being formed. Due to the doppler shifting by local oscillator 524, the pattern changes periodically in time at the frequency of local oscillator 524. Therefore, the signal derived by each particular photodetector of array 518 has the frequency of local oscillator 524, but has a relative phase and amplitude determined by the object information picked up by that particular photodetector of the array. These object information signals and the reference signal of the frequency of local oscillator 524 are applied to coherent detectors 542, after which the signals are processed and imaged as described in FIG. 1.

What is claimed is:

1. A wave-energy imaging system comprising a circumferential array of $n$ wave-energy transducers spaced at predetermined points about the circumference of a circle defining an aperture of many wavelengths in diameter, means for illuminating an object to be imaged with $m$ different characteristic coherent components of wave energy and at the same time generating an individual reference signal component for each of said $m$ components of said coherent wave energy, said illuminated object deriving an individual object-information coherent component of said wave energy for each of said $m$ different characteristic components, said aperture being within the path of all said object-information coherent components of said wave energy so that a separate object-information component signal is derived by each of said $n$ transducers for each of said $m$ individual object-information coherent components of said wave energy, $n$ coherent detection means each of which is respectively coupled to a corresponding one of said $n$ transducers, each of said $m$ components of said reference signal being applied to all $n$ of said coherent detection means, whereby each of said $n$ coherent detection means derives output signals manifesting real and imaginary coefficients of a complex number for each of said $m$ object-information component signals applied to that coherent detection means from the transducer corresponding thereto, said coefficients defining the relative phase and amplitude of each of said $m$ object information coherent components of wave energy for each of said $n$ transducers, and signal processing means responsive to the output signals from said coherent detection means for deriving with a given resolution the relative intensity at image points whose wavefronts fall on said entire aperture.

2. The system defined in claim 1, wherein said means for illuminating said object includes means for generating a single coherent frequency of wave energy, a moveable diffuser for diffusing said single coherent frequency of wave energy and control means for moving said moveable transducer between successive ones of a series of $m$ sequential exposures of said object by illuminating wave energy, whereby each one of said sequential exposures corresponds to a separate one of said $m$ different characteristic components.

3. The system defined in claim 1, wherein said means for illuminating said object includes means for generating in parallel wave energy composed of $m$ different, simultaneously-occurring, coherent frequencies of wave energy, whereby each one of said $m$ frequencies corresponds to a separate one of said $m$ different characteristic components.

4. The system defined in claim 1, wherein the diameter of said array aperture is in the order of 100 wavelengths.

5. The system defined in claim 1, wherein said wave energy is acoustic wave energy.

6. The system defined in claim 5, further including a coupling unit comprising a fluid-filled housing terminated in a diaphragm, said circumferential array of transducers being located in said fluid; and wherein said means for illuminating an object comprises an illuminating transducer located in said fluid at a position which is substantially equidistant from each of the $n$ transducers of said array, said illuminating transducers generating coherent acoustic wave energy of a given frequency in said fluid in response to an electrical signal of said given frequency being applied thereto, a moveable acoustic diffuser situated in said fluid between said illuminating transducer and said diaphragm, and a control means for moving said acoustic diffuser.

7. The system defined in claim 5, wherein said circumferential array comprises geophones located on the surface of the ground, and wherein said means for illuminating said object comprises a plurality of repeating charges randomly placed on the surface of the ground within the aperture of said array, and control means for sequentially firing sets of the repeating charges in turn to generate a train of successive explosions resulting in underground seismic waves in response to the firing of each respective one of the repeating charges, said train of successive explosions occurring at a predetermined coherent repetition rate.

8. The system defined in claim 1, wherein said wave energy is electromagnetic energy.

9. The system defined in claim 8, wherein said transducers of said circumferential array are microwave antennas, and wherein said means for illuminating said object comprises antenna means for transmitting an illuminating beam of coherent microwave energy in response to a microwave signal being applied thereto.

10. The system defined in claim 8, wherein said transducers of said circumferential array are square-law photodetectors, and wherein said means for illuminating said object includes means for generating coherent wave energy at a given optical frequency, means for splitting said optical frequency coherent wave energy into separate first and second beams, means for illuminating said object with said first beam so as to derive an object-information beam of wave energy which is incident on said array of photodetectors, means for generating a coherent modulating signal at a second frequency below the optical spectrum and deriving a reference signal at said second frequency, modulating means having said second beam and said modulating signal applied thereto for deriving a modulated optical wave energy output beam having an instantaneous optical frequency which is shifted from said given optical frequency by an amount which is substantially proportional to the instaneous amplitude of said modulating signal, and means for illuminating the photodetectors of said array with said modulated optical wave energy output beam, whereby said object-information beam of wave energy and said modulated optical wave energy output beam incident on said array form an interference pattern which changes in accordance with said second frequency and each of said transducers derives an individual object-information signal at said second frequency, and means for applying said reference signal and the object-information signal from each respective photodetector to the individual one of the $n$ coherent detection means corresponding thereto.

11. The system defined in claim 10, wherein a series of $m$ sequential exposures of said object are made, and wherein said means for illuminating the photodetectors of said array with said modulated optical wave energy output beam includes a phase shifter for randomly shifting the phase of said modulated optical wave energy output beam between successive ones of said $m$ sequential exposures.

12. A wave energy method for imaging an object comprising the steps of illuminating an object located in an object plane a given distance from and whose energy falls within the aperture of a circumferential array of $n$ spaced transducers with an illuminating beam of coherent wave energy to obtain an object information beam of said wave energy which is incident on said transducers of said array to thereby derive an individual object information signal from each of said $n$ transducers, coherently detecting each respective one of said object information signals against a common reference signal to obtain two outputs for each one of said $n$ transducers corresponding respectively to the real and imaginary coefficients of a complex number defining the relative amplitude and phase of the object-information beam wave energy incident on that transducer, and processing all the coherently detected outputs to derive a signal manifesting the relative amplitude of the image of said object at each of predetermined sample points distributed over the entire aperture.

13. The method defined in claim 12, wherein said processing step comprises the steps of:

a. selecting each respective one of said predetermined sample points in turn, b. subtracting an appropriate one of a set of predetermined phase shifts for the then-selected sample point from the coherently-detected outputs of each one of said $n$ transducers to effectively transform the object plane distance for the then-selected sample point to infinity, c. obtaining and then summing the members of an individual set of a predetermined plural number of orders of a given Bessel function squared of the phase-shifted coherently-detected output corresponding to each different one of said $n$ transducers, said given Bessel function being obtained by adding a phase function of the angular position of that transducer in said circumferential array to each coherently-detected output and summing the resultant $n$ complex numbers to obtain a processed signal corresponding to the relative amplitude of the image at the then-selected sample point, d. storing said processed signal at a location individually corresponding to the then-selected sample point, and e. repeating steps (b) through (d) for the next-selected sample point.

14. The method defined in claim 13, further including the step of displaying an image of said object in accordance with the processed signals stored at said locations.

15. The method defined in claim 13, wherein said illuminating step comprises the steps of sequentially illuminating said object $m$ times with diffused coherent wave energy, with the diffusion of said coherent wave energy being different, each of said $m$ times, to thereby provide a series of $m$ exposures of said object, wherein steps (a) through (e) are repeated during each of said $m$ exposures, whereby the processed signal stored at each location at the end of said $m$ exposures is proportional to the sum of the individual processed signals for that location obtained during each of said $m$ exposures.

* * * * *